United States Patent [19]

Oshimura et al.

[11] Patent Number: 5,854,199
[45] Date of Patent: Dec. 29, 1998

[54] CLEANING COMPOSITIONS CONTAINING ACYLATED DIPEPTIDES AND ACYLATED AMINO ACIDS

[75] Inventors: Eiko Oshimura; Hideki Yoshihara; Kazutami Sakamoto, all of Kawasaki; Tatsuya Hattori, Yokkaichi, all of Japan

[73] Assignee: Ajinomoto Co., Inc., Tokyo, Japan

[21] Appl. No.: 921,518

[22] Filed: Sep. 2, 1997

[30] Foreign Application Priority Data

Aug. 30, 1996 [JP] Japan .................................. 8-230698

[51] Int. Cl.$^6$ ............................... C11D 1/37; C11D 1/88; C07C 237/52
[52] U.S. Cl. ............................... 510/501; 554/37
[58] Field of Search ................. 510/501; 554/37

[56] References Cited

U.S. PATENT DOCUMENTS

| 4,116,768 | 9/1978 | Isowa et al. ........................... 195/29 |
| 5,120,463 | 6/1992 | Bjork et al. ..................... 252/174.12 |
| 5,393,468 | 2/1995 | Erilli et al. ............................. 252/550 |
| 5,427,711 | 6/1995 | Sakaguchi et al. ............. 252/174.25 |
| 5,444,041 | 8/1995 | Owen et al. ............................ 514/2 |
| 5,688,290 | 11/1997 | Bjork et al. ............................. 8/401 |

*Primary Examiner*—Paul Lieberman
*Assistant Examiner*—John R. Hardee
*Attorney, Agent, or Firm*—Oblon, Spivak, McClelland, Maier & Neustadt, P.C.

[57] ABSTRACT

A cleansing composition containing a N-long-chain-acylated dipeptide and an N-long-chain-acylated acidic amino acid. The cleansing composition exhibits low skin irritation, excellent resistance to hard water, is free from turbidity and the unpleasant odor associated with some natural peptides. The composition also provides excellent skin and hair feel qualities during and after use.

17 Claims, No Drawings

CLEANING COMPOSITIONS CONTAINING ACYLATED DIPEPTIDES AND ACYLATED AMINO ACIDS

BACKGROUND OF THE INVENTION

1. Field of the Invention

The present invention relates to a wash composition containing (A) an N-long-chain-acylated dipeptide in which the dipeptide moiety is composed of two acidic amino acids and (B) an N-long-chain-acylated acidic amino acid. The wash composition of the present invention is non-irritating to the skin, has a high resistance to hard water, and provides a pleasant feeling upon use, without leaving the hair feeling unlubricated during rinsing or the skin feeling stretched after washing.

2. Discussion of the Background

Anionic surface active agents such as alkylbenzenesulfonates, higher alcohol sulfates, polyoxyethylene alkyl ether sulfonates and the like have been widely used as surface active agent in wash compositions. Wash compositions composed mainly of these anionic surface active agents exhibit excellent cleaning ability, but do not provide a satisfactory sensory feeling during use. These substances produce a dry and hard feeling during rinsing, a rough feeling after use and the like, and cause significant skin irritation and damage to the hair. Higher fatty acid-type and phosphate ester-type surface active agents, which produce relatively little skin irritation, have been hitherto used. These surface active agents, however, have a low resistance to hard water and are easily bound to calcium in water, whereby a water-insoluble calcium salt (scum) is formed during rinsing. This interaction with calcium ions causes a decrease in bubbling and a decrease in bubble stability, as well as poor sensory feelings such as a dry and hard feeling of the hair and a rough feeling of the hair during rinsing.

In recent years, N-acyl acidic amino acid salts, which exhibit a low skin irritation, an excellent washability and an excellent feeling during use, have been widely used in wash compositions. The N-long-chain-acyl acidic amino acid salts have excellent solution stability in the weakly acidic pH range, which is mild to skin, exhibit less stretching feeling of the skin after use and are less irritating to the skin. On the other hand, as to the N-long-chain-acyl neutral amino acid salts, crystals are liable to separate out in the weakly acidic range, so that it is difficult to maintain the solution stability, and bubbling property is remarkably reduced in this pH range.

The N-long-chain-acyl acidic amino acid salts are also known to have relatively excellent resistance to hard water, but they do not have satisfactory skin and hair feel effects. Additionally, these materials leave hair feeling unlubricated during washing, i.e, there is a "tacky" feeling when one runs their fingers through their hair during rinsing, much like washing hair with soap or a synthetic dishware or textile detergent, for example. Consequently, the development of a wash composition which retains the advantages of N-long-chain-acyl acidic amino acid salts such as low skin irritation, high resistance to hard water and failure to produce the undesirable unlubricated feeling when rinsing hair, has been in demand.

Meanwhile, N-long-chain-acyl peptides formed by acylating peptides obtained by hydrolysis of natural proteins with higher fatty acids are also known as starting materials for a wash composition having a low skin irritation. These N-long-chain-acyl peptides are used, in many cases, to improve the bubbling property of a wash composition. These compounds can also be used to improve the resistance to hard water. Japanese Laid-Open (Kokai) No. 101,200/1983 discloses that a wash powder containing a higher fatty acid soap and a specific acyl peptide is excellent in scum dispersibility. Further, Japanese Laid-Open (Kokai) No. 65,197/1989 discloses that a wash composition containing a mono-salt of an acylated collagen peptide higher fatty acid is effective for removing metallic ions adhered to the hair because a carboxylic acid side chain of an acidic amino acid residue of the peptide forms a salt with the metallic ions.

However, these N-long-chain-acyl peptides are formed by acylating a mixture of peptides resulting from the hydrolysis of natural proteins. When they are mixed with a liquid wash, the resulting product becomes turbid or has a peculiar odor. Further, solution stability in weakly acidic range is not good as compared to N-long-chain-acyl acidic amino acid salts, and the resistance to hard water is not necessarily satisfactory.

Japanese Laid-Open (Kokai) No. 84,994/1984 proposes an N-(N'-long-chain-acylglycyl) glycine salt to conquer the problems, such as a turbidity, an odor and the like, associated with products formed by acylating natural proteins, and some wash compositions containing such N-long-chain-acyl neutral amino acid dipeptide salts have been proposed [see Japanese Laid-Open (Kokai) Nos. 51, 356/1993, 78, 693/1993 and 188, 694/1995]. With respect to the hard water resistance of these N-long-chain-acyl neutral amino acid dipeptide salts, Japanese Laid-Open (Kokai) No. 152,999/1984 discloses that the above-mentioned N-(N'-long-chain-acylglycyl)glycine salt exhibits excellent bubbling in both hard and soft water. However, the resistance to hard water of N-long-chain-acyl neutral amino acid dipeptide salts including N-(N'-long-chain-acylglycyl)glycine salts is not altogether satisfactory, and solution stability in the weakly acidic pH range is not sufficient.

SUMMARY OF THE INVENTION

It is an object of the present invention to provide a cleansing composition containing N-long-chain-acyl acidic amino acids that is suitable for washing skin and hair and which may: be non-irritating to the skin, have high resistance to hard water, be free from turbidity and the objectionable odor associated with some natural peptides, and leave hair and skin feeling soft and moisturized.

The present inventors have discovered that a wash composition containing an N-acylated acidic amino acid dipeptide and an N-long-chain-acylated acidic amino acid provides the above-mentioned properties. This finding has led to the completion of the present invention.

The objects of the present invention may be accomplished with a cleansing composition containing:

(A) an N-long-chain-acylated dipeptide represented by formula (1):

$$R^1\text{—CO—}(X\text{—}Y)\text{—OM}^1 \qquad (1),$$

where

X and Y are each, independently, an acidic amino acid residue, $R^1$ is a linear or branched alkyl or alkenyl group having from 7 to 21 carbon atoms, and $M^1$ is a hydrogen atom, an alkali metal ion, an ammonium ion, an alkylammonium ion, an alkanolammonium ion or a protonated basic amino acid; and (B) an N-long-chain-acyl acidic amino acid or a salt thereof.

The objects of the present invention are also accomplished with a process of cleansing skin, hair, or both, with the composition containing (A) and (B).

A more complete appreciation of the invention and many of the attendant advantages thereof will be readily obtained as the same becomes better understood by reference to the following detailed description.

DETAILED DESCRIPTION OF THE INVENTION

The cleansing composition of the present invention contains at least components (A) and (B) and preferably exhibits little to no skin irritation, has a high resistance to hard water, is free from a turbidity and the odor associated with natural peptides, does not leave hair unlubricated or tacky during rinsing of hair, and does not leave the skin feeling dried and stretched after use.

X and Y of the N-long-chain-acyl dipeptide of formula (1), which is component (A) of the cleansing composition of the present invention, are each acidic amino acid residues, and these may be the same or different. The term "residue" means that the amino group of X forms an amide group with the acyl group containing $R^1$ (e.g., $R^1CO$—NH—), and the carboxyl group of X forms an amide group with the amino group of Y (e.g., —CO—NH—). Both X and Y each have at least one side-chain which contains at least one carboxylic acid group (e.g., —$CO_2M^1$). Preferable examples of these acidic amino acid residues include glutamic acid and aspartic acid. Either L- or D-stereoisomers may be used. L-glutamic acid and L-aspartic acid residues are preferred.

In a preferred embodiment, X and Y are each, independently, a glutamic acid or an aspartic acid residue. When X is a glutamic acid residue, the peptide linkage (i.e., amide bond) with Y through the carboxyl group may be provided through either the α-carboxyl group or the γ-carboxyl group. When X is an aspartic acid residue, the peptide linkage with Y through the carboxyl group may be provided through either the α-carbonyl group or the β-carbonyl group. Specific examples of X are shown below:

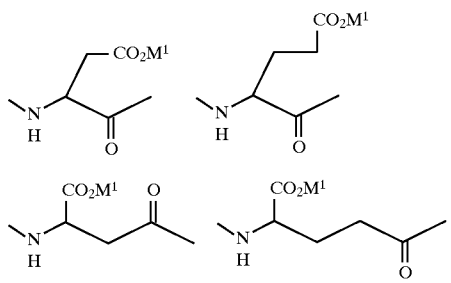

$R^1$ in the N-long-chain-acyl dipeptide of formula (1) is a linear or branched alkyl or alkenyl group having from 7 to 21 carbon atoms. In this invention, the term "branched alkyl group" includes groups which contain one or more cyclic moieties therein. Alkenyl groups have one or more double bonds, e.g., one, two, three or four double bonds. A linear or branched saturated or unsaturated acyl group having from 7 to 17 carbon atoms is preferable. The long-chain-acyl residue $R^1CO$— which contains the alkyl or alkenyl group can be introduced from fatty acids such as lauric acid, myristic acid, palmitic acid, stearic acid, arachidic acid, coconut oil fatty acid, hardened tallow fatty acid, behenic acid, isostearic acid, oleic acid, castor oil fatty acid, olive oil fatty acid, palm oil fatty acid, and mixtures thereof.

$M^1$ in the dipeptide of formula (1) may be hydrogen. Alternatively, $M^1$ may be an metal ion (e.g., an alkali metal, such as sodium or potassium), an ammonium ion, an alkyl ammonium ion (primary, secondary, tertiary or quanternary) or an alkanolammonium (primary, secondary, tertiary or quarternary) ion (e.g., triethanolamine). Alkyl groups or moieties in the ammonium ions may have from 1 to 30 carbon atoms. $M^1$ may also be a protonated basic amino acid, such as lysine and arginine. In the context of the present invention, when a compound has two or more $M^1$ groups they are each independently selected. As discussed above, the acidic amino acid residues X and Y in the N-long-chain-acyl dipeptide of formula (1) have carboxyl groups as side chains, and these carboxyl groups, independently from each other, may form the above-mentioned salts or be carboxylic acids. These salts may be used either singly or in combination.

The N-long-chain-acyl dipeptide of formula (1) or a salt thereof may easily be produced by, for example, a method in which a dipeptide containing an acidic amino acid is formed, and then acylated with a fatty acid halide in an alkaline aqueous solution. The dipeptide can be formed by any well-known method in peptide chemistry. Further, it can also be easily produced also by a method in which a N-long-chain-acyl amino acid and a carboxyl-protected amino acid are condensed using a condensing agent such as DCC (dicyclohexylcarbodiimide) or the like, and the carboxyl protective group is then selectively removed, or a method in which a N-long-chain-acyl amino acid is then converted to an acid halide using a halogenating agent such as an acid chloride or the like, and this halide is condensed with an amino acid. The amino acid residues X and Y may have either the L- or D-configuration. X and Y may both have the L-configuration or the D-configuration. Alternatively, X may have the L-configuration and Y may have the D-configuration, and vice versa.

Examples of the N-long-chain-acyl dipeptide of formula (1) include N-(N'-long-chain-acyl-α-glutamyl)glutamic acid, N-(N'-long-chain-acyl-γ-glutamyl)glutamic acid, N-(N'-long-chain-acyl-α-aspartyl)aspartic acid, N-(N'-long-chain-acyl-γ-aspartyl)aspartic acid, N-(N'-long-chain-acyl-α-glutamyl)aspartic acid, N-(N'-long-chain-aspartyl-γ-glutamyl)aspartic acid, N-(N'-long-chain-acyl-α-aspartyl)glutamic acid, N-(N'-long-chain-acyl-β-aspartyl)glutamic acid, and salts thereof. These N-long-chain-acyl dipeptides may be either racemic compounds or optically active compounds. The optical purity can range, therefore, from 0 to 100% ee.

One particularly preferred example of dipeptide (A) is represented by formula (2):

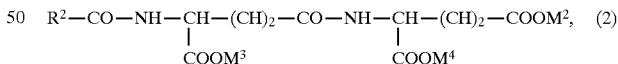

where $R^2$ is a linear or branched alkyl or alkenyl group having from 7 to 21 carbon atoms, and $M^2$, $M^3$ and $M^4$ are each, independently, hydrogen, an alkali metal, an ammonium ion, an alkylammonium ion, an alkanolammonium ion or a protonated basic amino. In a preferred embodiment, $R^2$ is the same as $R^1$, described above.

Component (B) of the present invention is an N-long-chain-acylated acidic amino acid. The amino acid residue of the N-long-chain-acylated acidic amino acid is preferably derived from glutamic acid, aspartic acid or the like. The acyl group is preferably a linear or branched saturated or unsaturated acyl group having from 8 to 22 carbon atoms, preferably from 8 to 18 carbon atoms. In a preferred embodiment, (B) is represented by the formula $R^1$—CO—(X)—$OM^1$, where $R^1$, X and $M^1$ are as defined above. The $R^1$ groups in formula (1) and the formula shown above are independently selected, and may be the same or different.

The above-mentioned acyl group may be introduced from fatty acids such as lauric acid, myristic acid, palmitic acid, stearic acid, arachidic acid, coconut oil fatty acid, hardened tallow fatty acid, behenic acid, isostearic acid, oleic acid, castor oil fatty acid, olive oil fatty acid, palm oil fatty acid, and mixtures thereof.

Examples of the salt of the N-long-chain-acyl acidic amino acid include salts of alkali metals such as sodium and potassium; salts of alkanolamines such as triethanolamine; salts of basic amino acids such as lysine and arginine; ammonium salts; and alkylammonium salts. The N-long-chain-acyl acidic amino acids and the salts thereof may be used either singly or in combination.

Examples of the N-long-chain-acyl acidic amino acid include N-lauroyl glutamic acid, N-myristoyl glutamic acid, N-palmitoyl glutamic acid, N-stearoyl glutamic acid, N-oleoyl glutamic acid, H-cocoyl glutamic acid, N-hardened tallow glutamic acid, N-lauroyl aspartic acid, N-myristoyl aspartic acid, N-palmitoyl aspartic acid, N-stearoyl aspartic acid, N-oleoyl aspartic acid, N-cocoyl aspartic acid, N-hardened tallow aspartic acid, and salts thereof. These N-long-chain-acyl acidic amino acids may be used in the form of both an optically active compound and a racemic compound. Therefore, the optical purity of the amino acid may be 0 to 100% ee.

The N-long-chain-acyl acidic amino acids and salts thereof can generally be formed by the method using the Schotten Baumann reaction in which an amino acid and a fatty acid halide are condensed in an alkaline aqueous solution, for example, the method described in Japanese Patent Publication Nos. 8,685/1971, 3,058/1973 and 38,681/1976. An amino acid to be acylated may be an L-isomer, a D-isomer or a racemic compound. Therefore, the optical purity of the amino acid may be 0 to 100% ee.

The amount of (A) in the cleansing composition may vary widely. The composition may contain 0.005 to 20% by weight of (A), based on the total weight of the composition. Preferably, the composition contains 0.01 to 15%, and, more preferably, 0.02 to 5% by weight of (A). These ranges include all specific values and subranges therebetween, including 0.05, 0.1, 0.2, 0.5, 1, 2 and 10% by weight of (A) in the composition.

The amount of (B) in the cleansing composition may vary widely. The composition may contain 1 to 80% by weight of (B), based on the total weight of the composition. Preferably, the composition contains 3 to 50%, and, more preferably 5 to 30% by weight of (B). These ranges include all specific values and subranges therebetween, including 2, 10, 15, 20, 25, 35, 40, 45, 50, 60 and 70% by weight of (B) in the composition.

The total amount of the N-long-chain-acyl dipeptide (A) and the N-long-chain-acyl acidic amino acid (B) in the wash composition of the present invention varies depending on the use. In order to provide a satisfactory washability, it is usually 5% by weight or more, preferably 10 to 80% by weight. However, the total amount of (A)+(B) may be less than 5% by weight (e.g., 1 to 4.5% by weight) or above 80% by weight (e.g., 81 to 100% by weight), depending on the use purpose of the wash composition. These ranges for the total amount of (A)+(B) include all specific values and subranges therebetween.

The ratio of the N-long-chain-acyl dipeptide (A) to the N-long-chain-acyl acidic amino acid (B) can vary widely, e.g., 0.1:100 to 5:1. The weight ratio is preferably between 0.1:100 and 20:100, more preferably between 0.5:100 and 10:100. When the ratio is less than 0.1:100, the effect of improvement on the resistance to hard water may be unsatisfactory. In addition, hair may have an unlubricated or tacky feeling during rinsing. When the ratio exceeds 20:100, the skin and or hair feel properties may be compromised, and, in addition the composition may not be economical to produce.

The wash composition of the present invention may contain other surface active agents to adjust the washability and the bubbling property without impairing the effect of the present invention. Examples of other surface active agents include anionic surface active agents such as higher fatty acid salts, alkyl sulfonates, alkylbenzene sulfonates, α-olefin sulfonates, polyoxyethylenealkyl ether sulfonates, N-acyl aminocarboxylates, polyoxyethylenealkyl ether carboxylates, alkyl ether phosphates and sulfosuccinic acids; ampholytic surface active agents such as alkylbetaine surface active agents, amidobetaine surface active agents, alkylsulfobetaine surface active agents, amidosulfobetaine surface active agents and imidazoline surface active agents; nonionic surface active agents such as sugar ether surface active agents, sugar amide surface active agents, sugar ester surface active agents, alkyl saccharide surface active agents, polyoxyethylenealkyl ether surface active agents, higher fatty acid alkanolamide surface active agents and amine oxide surface active agents; and cationic surface active agents such as benzalkonium chloride, a monoallyl quaternary ammonium salt, a diallyl quaternary ammonium salt, an N-α-acylarginine lower allyl ester salt and an N-ε-alkyl lysine lower alkyl ester salt. These surfactants may have 8 to 100 carbon atoms, preferably 8 to 50 carbon atoms, more preferably 8 to 30 carbon atoms and, most preferably, 8 to 20 carbon atoms. Further, surface active agents having a low resistance to hard water, such as higher fatty acids or salts thereof, can improve the resistance to hard water by mixing the same with the wash composition of the present invention. That is, it is possible to provide a wash composition comprising a higher fatty acid or its salt as component (C) in addition to the N-long-chain-acyl dipeptide of formula (1) or its salt as component (A) and the N-long-chain-acyl acidic amino acid or its salt as component (B). In this case as well, the amount (weight %) of the higher fatty acid or its salt as component (C) is at most 30% based on the total amount of components (A), (B) and (C) in order to exhibit high resistance to hard water. Specific ranges for the weight percent of (C) in the composition include 0.1 to 30%, 1 to 30%, and 5 to 25% by weight. These weight percent ranges include all specific values and subranges therebetween.

The wash composition of the present invention may also contain other components that are commonly used in wash compositions without impairing the effects of the present invention. Examples thereof include water-soluble high-molecular compounds such as methyl cellulose, hydroxycellulose, hydroxyethyl cellulose and hydroxypropylmethyl cellulose, wetting agents such as propylene glycol, glycerol, 1,3-butylene glycol, polyethylene glycol and sorbitol; viscosity modifiers such as methyl cellulose, ethyl cellulose, hydroxyethyl cellulose, carboxyvinyl polymer, xanthane gum, guar gum, ethanol, polyoxyethylene glycol distearate and polyoxyethylene sorbitan tristearate; hydrocarbons such as liquid paraffin, solid paraffin, vaseline, squalane and olefin oligomer; emulsifiers such as glycerol monoalkyl ester, glycerol monostearate, polyoxyethylenesorbitan monolaurate, polyoxyethylenecetyl ether and polyoxyethylene stearate; higher alcohols such as lauryl alcohol, cetyl alcohol, stearyl alcohol and behenyl alcohol; oils such as a mint oil, an olive oil, a castor oil, a yolk oil, a camellia oil, a soybean oil, a linseed oil, an avocado oil, a jojoba oil and lanolin; ester oils such as isopropyl myristate, isopropyl palmitate, stearyl stearate, octyldodecyl myristate and octyldodecyl oleate; pearling agents such as ethylene glycol distearate and styrene polymer, antiseptics such as methyl paraben and butyl paraben; UV absorbers such as benzophenone derivatives and benzotriazole derivatives; disinfectants such as triclosan: anti-inflammatories such as dipotassium glycyrrhetinate and tocopherol acetate; dandruff preventing agents such as zinc pyrithione; amino acids; drugs; pH adjustors; flavors; pigments; and antioxidants.

Having generally described this invention, a further understanding can be obtained by reference to certain specific examples which are provided herein for purposes of illustration only and are not intended to be limiting unless otherwise specified.

EXAMPLES

Production Example 1

A suspension of 20 g (0.0724 mols) of α-glutamylglutamic acid in 70 ml of water was dissolved in a 27-% sodium hydroxide aqueous solution until the pH reached 11, and 35 ml of acetone were added thereto. To the solution were added dropwise 15.8 g (0.0724 mols) of lauroyl chloride over a period of 1 hour. When adding lauroyl chloride, the temperature was maintained at 10° C., and 27-% sodium hydroxide was added dropwise simultaneously to keep the pH constant. After the addition of lauroyl chloride, the reaction solution was warmed at 30° C., and allowed to stand for 30 minutes. Subsequently, the pH was adjusted to 1 with the addition of conc. hydrochloric acid. The solid precipitate was separated by filtration, and dried to obtain 30.6 g of N-(N'-lauroyl-α-glutamyl)glutamic acid in a yield of 92%. This solid was analyzed by infrared spectrophotometry. A peak diagnostic of an amide group was observed at 1,650 cm$^{-1}$ and a peak diagnostic of a carboxyl group was observed at 1,730 cm$^{-1}$, respectively.

Production Example 2

A suspension of 30 g (0.121 mols) of α-aspartylaspartic acid in 115 ml of water was dissolved in a 27-% sodium hydroxide aqueous solution until the pH reached 11, and 58 ml of acetone were added thereto. To the solution were added dropwise 26.9 g (0.121 mols) of cocoyl chloride over a period of 1 hour. When adding cocoyl chloride, the temperature was maintained at 10° C., and 27-% sodium hydroxide was added dropwise simultaneously to keep the pH at 11. After the addition of cocoyl chloride, the reaction solution was warmed at 30° C., and allowed to stand for 30 minutes. Subsequently, the pH was adjusted to 1 with the addition of conc. hydrochloric acid. The solid precipitate was separated by filtration, and dried to obtain 47.2 g of N-(N'-cocoyl-α-aspartyl)aspartic acid in a yield of 90%. This solid was analyzed by infrared spectrophotometry. A peak diagnostic of an amide group was observed at 1,640 cm$^{-1}$ and a peak diagnostic of a carboxyl group was observed at 1,730 cm$^{-1}$, respectively.

Production Example 3

A suspension of 20 g (0.081 mols) of α-aspartylaspartic acid in 80 ml of water was dissolved in a 27-% sodium hydroxide aqueous solution until the pH reached 11, and 40 ml of acetone were added thereto. To the solution were added dropwise 17.7 g (0.081 mols) of lauroyl chloride over a period of 1 hour. When adding lauroyl chloride, the temperature was maintained at 10° C., and 27-% sodium hydroxide was added dropwise simultaneously to keep the pH at 11. After the addition of lauroyl chloride, the reaction solution was warmed at 30° C., and allowed to stand for 30 minutes. Subsequently, the pH was adjusted to 1 with the addition of conc. hydrochloric acid. The solid precipitate was separated by filtration, and dried to obtain 31.7 g of N-(N'-lauroyl-α-aspartyl)aspartic acid in a yield of 91%. This solid was analyzed by infrared spectrophotometry. A peak diagnostic of an amide group was observed at 1,640 cm$^{-1}$ and a peak diagnostic of a carboxyl group was observed at 1,730 cm$^{-1}$, respectively.

Production Example 4

A suspension of 16 g (0.058 mols) of γ-glutamylglutamic acid in 55 ml of water was dissolved in a 27-% sodium hydroxide aqueous solution until the pH reached 11, and 27 ml of acetone were added thereto. To the solution were added dropwise 12.6 g (0.058 mole) of lauroyl chloride over a period of 1 hour. When adding lauroyl chloride, the temperature was maintained at 10° C., and 27-% sodium hydroxide was added dropwise simultaneously to keep the pH at 11. After the completion of the addition of lauroyl chloride, the reaction solution was warmed at 30° C., and allowed to stand for 30 minutes. Subsequently, the pH was adjusted to 1 with the addition of conc. hydrochloric acid. The solid precipitate was separated by filtration, and dried to obtain 23.6 g of N-(N'-lauroyl-γ-glutamyl)glutamic acid in a yield of 89%. This solid was analyzed by infrared spectrophotometry. A peak diagnostic of an amide group was observed at 1,640 cm$^{-1}$ and a peak diagnostic of a carboxyl group was observed at 1,730 cm$^{-1}$, respectively. FAB mass spectrum: 459 (MH$^+$).

Production Example 5

Production Example 1 was repeated using 20.0 g (0.072 mols) of α-glutamylglutamic acid and 21.9 g (0.072 mols)of stearoyl chloride to give 34.9 g of N-(N'-stearoyl-α-glutamyl)glutamic acid in a yield of 89%. This solid was analyzed by infrared spectrophotometry. A peak diagnostic of an amide group was observed at 1,650 cm$^{-1}$ and a peak diagnostic of a carboxyl group was observed at 1,730 cm$^{-1}$, respectively.

Production Example 6

Production Example 1 was repeated using 20.0 g (0.072 mols) of α-glutamylglutamic acid and 16.1 g (0.072 mols) of cocoyl chloride to give 80.1 g of N-(N'-cocoyl-α-glutamyl)glutamic acid in a yield of 90%. This solid was analyzed by infrared spectrophotometry. A peak diagnostic of an amide group was observed at 1,640 cm$^{-1}$ and a peak diagnostic of a carboxyl group was observed at 1,730 cm$^{-1}$, respectively.

In the following examples, N-long-chain-acyl peptides were used by forming salts with triethanolamine solution, sodium hydride solution or potassium hydride solution. When a triethanolamine salt was formed, the pH was adjusted to 5.2. When a sodium salt or potassium salt was formed, the pH was adjusted to 5.8. In the following Test Example 1–5, the sodium salt of N-long-chain acylpeptide was used with the sodium salt of the N-long-chain-acyl acidic amino acid, and the triethanolamine salt of the N-long-chain acylpeptide was used with the triethanolamine salt of the N-long-chain-acyl acidic amino acid.

Test Example 1

Test for bubbling property:

Each wash composition including N-long-chain-acyl acidic amino acid salt (0.5% by weight) and the N-long-chain-acyl dipeptide salt was prepared. 50 ml of this solution was stirred for 5 seconds using a domestic mixer ("Millser", trade name for a device produced by Iwatani International Corporation), and allowed to stand for 1 minute. Then the amount (ml) of bubbles was measured. City water (calcium concentration 20 ppm) was used to prepare the aqueous solution. When the N-long-chain-acyl acidic amino acid forms a water-insoluble salt with calcium in an aqueous solution, the bubbling property is decreased. The results are shown in Tables 1–4.

TABLE 1

Bubbling property

| | | comparative example | Examples | | |
|---|---|---|---|---|---|
| Ratio of N-N'-lauroyl-α-glutamyl) glutamic acid salt to N-long-chain-acyl acidic amino acid salt | | 0% | 0.5% | 5% | 10% |
| Amount of bubbles (ml) | Triethanolamine N-cocoyl glutamate | 180 (193) | 187 | 195 | 195 |
| | Sodium N-cocoyl glutamate | 133 (198) | 160 | 175 | 190 |
| | Triethanolamine N-lauroyl aspartate | 179 (203) | 187 | 197 | 203 |
| | Sodium N-lauroyl aspartate | 173 (253) | 200 | 215 | 238 |

Values in parentheses are amount of bubbles (ml) using ion-exchanged water (>18MΩ).

TABLE 2

Bubbling property

| | | comparative example | Examples | | |
|---|---|---|---|---|---|
| Ratio of N-N'-lauroyl-γ-glutamyl) glutamic acid salt to N-long-chain-acyl acidic amino acid salt | | 0% | 0.5% | 5% | 10% |
| Amount of bubbles (ml) | Triethanolamine N-cocoyl glutamate | 180 (193) | 185 | 188 | 193 |
| | Sodium N-cocoyl glutamate | 133 (198) | 155 | 195 | 200 |
| | Triethanolamine N-lauroyl aspartate | 180 (203) | 188 | 195 | 200 |
| | Sodium N-lauroyl aspartate | 173 (253) | 190 | 230 | 235 |

Values of parentheses are amount of bubbles (ml) using ion-exchanged water (>18MΩ).

TABLE 3

Bubbling property

| | | comparative example | Examples | | |
|---|---|---|---|---|---|
| Ratio of N-N'-lauroyl-α-aspartyl) aspartic acid salt to N-long-chain-acyl acidic amino acid salt | | 0% | 0.5% | 5% | 10% |
| Amount of bubbles (ml) | Triethanolamine N-cocoyl glutamate | 180 (193) | 185 | 190 | 190 |
| | Sodium N-cocoyl glutamate | 133 (198) | 140 | 193 | 205 |
| | Triethanolamine N-lauroyl aspartate | 180 (203) | 185 | 195 | 200 |
| | Sodium N-lauroyl aspartate | 173 (253) | 190 | 223 | 240 |

Values of parentheses are amount of bubbles (ml) using ion-exchanged water (>18MΩ).

TABLE 4

Bubbling property

| | | comparative example | Examples | | |
|---|---|---|---|---|---|
| Ratio of coconut oil fatty acid acyl hydrolysis collagen salt to N-long-chain-acyl acidic amino acid salt | | 0% | 0.5% | 5% | 10% |
| Amount of bubbles (ml) | Triethanolamine N-cocoyl glutamate | 185 (193) | 180 | 190 | 180 |
| | Sodium N-cocoyl glutamate | 133 (198) | 140 | 143 | 150 |
| | Triethanolamine N-lauroyl aspartate | 187 (203) | 140 | 118 | 95 |
| | Sodium N-lauroyl aspartate | 173 (253) | 175 | 167 | 87 |

Values of parentheses are amount of bubbles (ml) using ion-exchanged water (>18MΩ).

Text Example 2

Tests for an unlubricated feeling during washing of hair:

Five liters of each wash composition (40° C.) including a N-long-chain-acyl acidic amino acid salt (0.5% by weight) and N-long-chain-acyl peptide salt were prepared using water with a calcium concentration adjusted to 100 ppm. Five panelists washed hair pieces (each 20 g net), and the hair feel properties during rinsing were evaluated according to four grades. The results are shown in Tables 5–7.

TABLE 5

| | | Comparative example | Examples | | |
|---|---|---|---|---|---|
| Ratio of N-N'-lauroyl-α-glutamyl) glutamic acid salt to N-long-chain-acyl acidic amino acid salt | | 0% | 0.5% | 5% | 10% |
| Unlubricated or tacky feeling of the hair | Triethanolamine N-cocoyl glutamate | Δ | ○ | ◎ | ◎ |
| | Sodium N-cocoyl glutamate | X | Δ | ◎ | ◎ |
| | Triethanolamine N-lauroyl aspartate | Δ | ○ | ◎ | ◎ |
| | Sodium N-lauroyl aspartate | X | Δ | ◎ | ◎ |

◎ There is no unlubricated or tacky feeling at all.
○ There is little unlubricated or tacky feeling.
Δ There is slight unlubricated or tacky feeling.
X There is an unlubricated or tacky feeling.

TABLE 6

| | | Comparative example | Examples | | |
|---|---|---|---|---|---|
| Ratio of N-N'-stearoyl-α-glutamyl) glutamic acid salt to N-long-chain-acyl acidic amino acid salt | | 0% | 0.5% | 5% | 10% |
| Unlubricated or tacky feeling of the | Triethanolamine N-cocoyl glutamate | Δ | ○ | ◎ | ◎ |
| | Sodium N-cocoyl glutamate | X | Δ | ◎ | ◎ |
| | Triethanolamine | Δ | ○ | ◎ | ◎ |

TABLE 6-continued

|  |  | Comparative example | Examples | | |
|---|---|---|---|---|---|
| hair | N-lauroyl aspartate Sodium N-lauroyl aspartate | X | Δ | ⊚ | ⊚ |

⊚ There is no unlubricated or tacky feeling at all.
○ There is little unlubricated or tacky feeling.
Δ There is slight unlubricated or tacky feeling.
X There is an unlubricated or tacky feeling.

TABLE 7

|  |  | Comparative example | Examples | | |
|---|---|---|---|---|---|
| Ratio of N-N'-cocoyl-α-aspartyl) aspartic acid salt to N-long-chain-acyl acidic amino acid salt | | 0% | 0.5% | 5% | 10% |
| Unlubricated or tacky feeling of the hair | Triethanolamine N-cocoyl glutamate | Δ | ○ | ⊚ | ⊚ |
| | Sodium N-cocoyl glutamate | X | Δ | ⊚ | ⊚ |
| | Triethanolamine N-lauroyl aspartate | Δ | ○ | ⊚ | ⊚ |
| | Sodium N-lauroyl aspartate | X | Δ | ⊚ | ⊚ |

⊚ There is no unlubricated or tacky feeling at all.
○ There is little unlubricated or tacky feeling.
Δ There is slight unlubricated or tacky feeling.
X There is an unlubricated or tacky feeling.

Test Example 3

Tests for adhesion of scum:

Five liters of each wash composition (40° C.) including a N-long-chain-acyl acidic amino acid salt (0.5% by weight) and N-long-chain-acyl acidic amino acid salt were prepared using water with a calcium concentration adjusted to 100 ppm in a washbowl in which a vinyl chloride black plate was attached to the inner wall surface such that the water level was situated in the center. Five panelists washed hair pieces (each 20 g net), and after the washing, the vinyl chloride plate was taken out, and the amount of scum adhered was evaluated according to five grades. The results are shown in Tables 8–10.

TABLE 8

|  |  | Comparative Example | Examples | | |
|---|---|---|---|---|---|
| Ratio of N-N'-lauroyl-α-glutamyl) glutamic acid to N-long-chain-acyl acidic amino acid salt | | 0% | 0.5% | 5% | 10% |
| Amount of scum | Triethanolamine - cocoyl glutamate | Δ | ○ | ⊚ | ⊚ |
| | Sodium N-cocoyl glutamate | X | Δ | ⊚ | ⊚ |
| | Triethanolamine - lauroyl aspartate | Δ | ○ | ⊚ | ⊚ |
| | Sodium N-lauroyl aspartate | X | Δ | ⊚ | ⊚ |

⊚ No adhered scum.
○ Little adhered scum.
Δ More adhered scum.
X Significant adhered scum.

TABLE 9

|  |  | Comparative Examples | | | |
|---|---|---|---|---|---|
| Ratio of N-(N'-lauroyl-glycyl) glycine acid salt to N-long-chain-acyl acidic amino acid salt | | 0% | 0.5% | 5% | 10% |
| Amount of scum | Triethanolamine N-cocoyl glutamate | Δ | Δ | Δ | ○ |
| | Sodium N-cocoyl glutamate | X | X | X | Δ |
| | Triethanolamine N-lauroyl aspartate | Δ | Δ | Δ | ○ |
| | Sodium N-lauroyl aspartate | X | X | X | Δ |

⊚ No adhered scum.
○ Little adhered scum.
Δ More adhered scum.
X Significant adhered scum.

TABLE 10

|  |  | Comparative Examples | | | |
|---|---|---|---|---|---|
| Ratio of coconut oil fatty acid acyl hydrolysis collagen salt to N-long-chain-acyl acidic amino acid salt | | 0% | 0.5% | 5% | 10% |
| Amount of scum | Triethanolamine N-cocoyl glutamate | Δ | Δ | Δ | ○ |
| | Sodium N-cocoyl glutamate | X | X | X | Δ |
| | Triethanolamine N-lauroyl aspartate | Δ | Δ | Δ | ○ |
| | Sodium N-lauroyl aspartate | X | X | X | Δ |

⊚ No adhered scum.
○ Little adhered scum.
Δ More adhered scum.
X Significant adhered scum.

Test Example 4

Odor test:

Each wash composition including N-long-chain-acyl acidic amino acid salt (30% by weight) and the N-long-chain-acyl dipeptide salt was prepared. After these solutions were stored at 40° C. for 1 week, the odor was examined. The results are shown in Table 11.

TABLE 11

|  | Examples | | | Comparative Examples | | |
|---|---|---|---|---|---|---|
| Ratio of N-(N'-lauroyl-α-glutamyl) glutamic acid to N-long-chain-acyl acidic amino acid salt | 0.5% | 5% | 10% | | | |
| Ratio of coconut oil fatty acid acyl hydrolysis collagen to N-long-chain-acyl acidic amino acid salt odor | | | | 0.5% | 5% | 10% |
| Triethanolamine N-cocoyl glutamate | ○ | ○ | ○ | Δ | Δ | X |
| Sodium N-cocoyl glutamate | ○ | ○ | ○ | Δ | X | X |
| Triethanolamine N-lauroyl aspartate | ○ | ○ | ○ | ○ | Δ | X |
| Sodium N-lauroyl aspartate | ○ | ○ | ○ | Δ | X | X |

○ There is no unpleasant odor.
Δ There is a slight unpleasant odor.
X There is a considerable unpleasant odor.

Example 5

Test for turbidity:

Each wash composition including N-long-chain-acyl acidic amino acid salt (30% by weight) and the N-long-chain-acyl dipeptide salt was prepared. After these solutions were stored at 0° C. for 1 week, the turbidity was examined. The results are shown in Table 12.

TABLE 12

|  | Examples | | | Comparative Examples | | |
|---|---|---|---|---|---|---|
| Ratio of N-(N'-lauroyl-α-glutamyl) glutamic acid to N-long-chain-acyl acidic amino acid salt | 0.5% | 5% | 10% | | | |
| Ratio of coconut oil fatty acid acyl hydrolysis collagen to N-long-chain-acyl acidic amino acid salt odor | | | | 0.5% | 5% | 10% |
| Triethanolamine N-cocoyl glutamate | ○ | ○ | ○ | ○ | Δ | X |
| Sodium N-cocoyl glutamate | ○ | ○ | ○ | Δ | X | X |
| Triethanolamine N-lauroyl aspartate | ○ | ○ | ○ | ○ | Δ | X |
| Sodium N-lauroyl aspartate | ○ | ○ | ○ | Δ | X | X |

○ There is no turbidity
Δ There is a slight turbidity
X There is a considerable turbidity

Formulation Example 1

A hair shampoo was prepared using the formulation shown in Table 13. This hair shampoo exhibited excellent bubbling in hard water, a low irritation to the skin and less unlubricated or tacky feeling during hair rinsing.

TABLE 13

Hair shampoo

| Composition | Content (%) |
|---|---|
| Triethanolamine N-(N'-lauroyl-α-glutamyl) glutamate | 0.5% |
| Triethanolamine N-(N'-lauroyl-γ-glutamyl) glutamate | 0.5% |
| Triethanolamine N-lauroyl glutamate | 18 |
| Triethanolamine lauryl sulfonate | 3 |
| Coconut oil fatty acid dimethylamino acetic acid betaine | 5 |
| Carboxy vinyl polymer | 4 |
| Coconut oil fatty acid diethanolamide | 2 |
| Cationized cellulose | 0.4 |
| Trimethyl glycine | 2 |
| Antiseptic | 0.2 |
| Water | Balance |

Formulation Example 2

A hair shampoo was prepared using the formulation shown in Table 14. This hair shampoo exhibited excellent bubbling in hard water, a low irritation to the skin and less unlubricated or tacky feeling during hair rinsing.

TABLE 14

Hair Shampoo

| Composition | Content (%) |
|---|---|
| Triethanolamine N-(N'-cocoyl-α-aspartyl) aspartate | 2 |
| Triethanolamine N-cocoyl aspartate | 20 |
| Coconut oil fatty acid diethanolamide | 4 |
| Cationized cellulose | 0.4 |
| POE (60) polymyristylene (1) tallow alkyl ether | 2.5 |
| Distearyl polyethylene glycol | 2 |
| Glycerol | 5 |
| Antiseptic | 0.2 |
| Perfume | 0.1 |
| Water | Balance |

Formulation Example 3

A cleansing cream was prepared using the formulation shown in Table 15. This cleansing cream exhibited excellent bubbling in hard water, a low irritation to skin and less stretching feeling of skin after washing.

TABLE 15

Cleansing cream

| Composition | Content (%) |
|---|---|
| Sodium N-(N'-cocoyl-α-glutamyl) glutamate | 24 |
| Arginine N-cocoyl glutamate | 10 |
| Sodium stearate | 1 |
| Coconut oil fatty acid diethanolamide | 4 |
| Distearyl polyethylene glycol | 2 |
| Sorbitol | 2 |
| Hydroxymethyl cellulose | 0.8 |
| POE (120) methyl glucose dioleate | 0.5 |
| Propylene glycol | 10 |
| Antiseptic | 0.2 |
| Perfume | 0.1 |
| Water | Balance |

Formulation Example 4

A body shampoo was prepared using the formulation shown in Table 16. This cleansing cream exhibited excellent bubbling in hard water, a low irritation to skin and less stretching feeling of skin after washing.

TABLE 16

Body Shampoo

| Composition | Content (%) |
|---|---|
| Potassium N-(N'-cocoyl-α-glutamyl glutamate | 6 |
| Arginine N-cocoyl glutamate | 15 |
| Coconut oil fatty acid potassium salt | 4 |
| Coconut oil fatty acid diethanolamide | 3 |
| Cationized guar gum | 1 |
| Butylene glycol | 3 |
| Citric acid mono hydrate | suitable amount |
| Antiseptic | 0.2 |
| Perfume | 0.1 |
| Water | Balance |

Obviously, additional modifications and variations of the present invention are possible in light of the above teachings. It is therefore to be understood that within the scope of the appended claims, the invention may be practiced otherwise than as specifically described herein.

This application is based on Japanese Application No. 230698/1996 filed on Aug. 30, 1996 and incorporated herein by reference in its entirety.

What is claimed as new and desired to be secured by Letters Patent of the United States is:

1. A cleansing composition, comprising:
   (A) an N-long-chain-acylated dipeptide represented by formula (1):

$$R^1-CO-(X-Y)-OM^1 \qquad (1),$$

wherein
   X and Y are each, independently, an acidic amino acid residue,
   $R^1$ is a linear or branched alkyl or alkenyl group having from 7 to 21 carbon atoms, and
   $M^1$ is a hydrogen atom, an alkali metal ion, an ammonium ion, an alkylammonium ion, an alkanolammonium ion or a protonated basic amino acid; and
   (B) a N-long-chain-acylated acidic amino acid or a salt thereof.

2. The cleansing composition of claim 1, wherein X is a glutamic acid residue.

3. The cleansing composition of claim 1, wherein X is an aspartic acid residue.

4. The cleansing composition of claim 1, wherein Y is a glutamic acid residue.

5. The cleansing composition of claim 1, wherein Y is an aspartic acid residue.

6. The cleansing composition of claim 1, comprising 0.005 to 20% by weight of (A).

7. The cleansing composition of claim 1, comprising 1 to 80% by weight of (B).

8. The cleansing composition of claim 1, comprising:
   0.005 to 20% by weight of (A); and 1 to 80% by weight of (B).

9. The cleansing composition of claim 1, wherein the weight ratio of (A) to (B) is 0.1:100 to 1:5.

10. A process for making the wash composition of claim 1 comprising combining (A) and (B).

11. A process for cleansing skin or hair, comprising applying the cleansing composition of claim 1 to the skin or hair.

12. The cleansing composition of claim 1, wherein (B) has the formula $$R^1-CO-(X)-OM^1,$$

where X is an acidic amino acid residue, $R^1$ is a linear or branched alkyl or alkenyl group having from 7 to 21 carbon atoms, and $M^1$ is a hydrogen atom, an alkali metal ion, an ammonium ion, an alkylammonium ion, an alkanolammonium ion or a protonated basic amino acid.

13. The cleansing composition of claim 1, wherein X and Y are each a glutamic acid residue.

14. The cleansing composition of claim 1, wherein X and Y are each an aspartic acid residue.

15. The cleansing composition of claim 1, comprising:
    0.01 to 15% by weight of (A); and 3 to 50% percent by weight of (B).

16. The cleansing composition of claim 1, comprising:
    0.02 to 5% by weight of (A); and 5 to 30% percent by weight of (B).

17. An N-long-chain-acylated dipeptide represented by formula (2):

$$R^2-CO-NH-\underset{\underset{COOM^3}{|}}{CH}-(CH)_2-CO-NH-\underset{\underset{COOM^4}{|}}{CH}-(CH)_2-COOM^2, \qquad (2)$$

wherein
$R^2$ is a linear or branched alkyl or alkenyl group having from 7 to 21 carbon atoms; and
$M^2$, $M^3$ and $M^4$ are each, independently, a hydrogen atom, an alkali metal ion, an ammonium ion, an alkylammonium ion, an alkanolammonium ion or a protonated basic amino acid.

* * * * *